United States Patent [19]

Wand et al.

[11] Patent Number: 5,061,814
[45] Date of Patent: Oct. 29, 1991

[54] HIGH TILT FERROELECTRIC LIQUID CRYSTAL COMPOUNDS AND COMPOSITIONS

[75] Inventors: Michael D. Wand; Rohini T. Vohra; David M. Walba, all of Boulder, Colo.

[73] Assignee: Displaytech, Inc., Boulder, Colo.

[21] Appl. No.: 359,991

[22] Filed: Jun. 1, 1989

[51] Int. Cl.$^5$ .................... C07D 303/12; C09K 19/34; C09K 19/12
[52] U.S. Cl. ................................. 549/560; 549/555; 549/561; 252/299.61; 252/299.65
[58] Field of Search ............... 252/299.01, 299.61, 252/299.65; 549/557, 560, 561, 555

[56] References Cited

U.S. PATENT DOCUMENTS 4,638,073  1/1987  Walba et al. .............. 252/299.61
4,835,295  5/1989  Walba et al. .............. 549/557

OTHER PUBLICATIONS

Ozaki et al. (1985) Jpn J. Appl. Phys. Part I 24, (Suppl. 24-3):63-65.
Walba et al. (1986) J. Amer. Chem. Soc. 108:7424-7425.
Hemmerling et al. (1988) European Patent Application, Publication No. 263437.
Ichihasi et al. (1988) European Patent Application, Publication No. 269-062.
Furukawa et al. (1988) European Patent Application, Publication No. 220747.

*Primary Examiner*—John S. Maples
*Assistant Examiner*—Philip Tucker
*Attorney, Agent, or Firm*—Greenlee and Associates

[57] ABSTRACT

Chiral nonracemic molecules which are useful in the preparation of high polarization density FLC compositions and which have the following structure are provided:

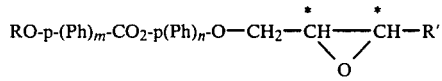

wherein Ph is a 1,4 substituted phenyl group, $m=2$ and $n=1$ or $m=1$ and $n=2$, asymmetric carbons are indicated by *. R is an alkyl group having three to fifteen carbon atoms, and R' is an alkyl group having one to seven carbons. The invention in particular provides compounds having the R,R or S,S configuration in the epoxide tail. The epoxy phenylbenzoates of this invention display a property of inducing a tilt angle greater than expected in FLC compositions in which they are combined.

24 Claims, 1 Drawing Sheet

HIGH TILT FERROELECTRIC LIQUID CRYSTAL COMPOUNDS AND COMPOSITIONS

This invention was made with partial support of the U.S. Government and it has certain rights in this invention.

FIELD OF THE INVENTION

The present invention relates in general to ferroelectric liquid crystal (FLC) materials and particularly to those which display smectic C* phases with high tilt angle or to those which induce high tilt angle when combined with low tilt FLC host materials. The FLC materials of the present invention also retain high polarization associated with fast switching speeds in FLC based devices.

BACKGROUND OF THE INVENTION

Electro-optic effects with sub-microsecond switching speeds can be achieved using the technology of ferroelectric liquid crystals (FLCs) of N. A. Clark and S. T. Lagerwall (1980) Appl. Phys. Lett. 36:899 and U.S. Pat. No. 4,367,924. These investigators have reported display structures prepared using FLC materials having not only high speed response (about 1,000 times faster than currently used twisted nematic devices), but which also exhibit bistable, threshold sensitive switching. Such properties make FLC based devices excellent candidates for light modulation devices including matrix addressed light valves containing a large number of elements for passive displays of graphic and pictorial information, optical processing applications, as well as for high information content dichroic displays.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the chiral molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. High switching speeds are then associated with FLC phases which possess high polarization density and low orientational viscosity.

Optics may provide an alternative to electronics in data communication and processing applications where high data rates are achieved through either high bandwidth channels or highly parallel processing. To this end a variety of devices for the generation and detection of intensity modulated light have been developed. However, the development of computer systems based on optics technology has been hindered by deficiencies in two key components: the optical crossbar switch and the spatial light modulator (SLM). Both of these components require a large number of light modulating elements, ideally rapidly switchable, in a small area. Envisioned systems could use crossbar switches with up to N=1000 lines, requiring between about $10^4$ [Nln(N)] to $10^6$ [$N^2$] switching elements, or SLMs with up to $N^2=10^6$ elements. Any switching element considered for these components must meet certain requirements. The individual switching elements must be small in size so that the complete device will not be unwieldily large. The elements must be cable of switching quickly so that the device can be reconfigured in a reasonable time. The elements should afford high contrast between the "on" and "off" states (>1000:1 required for a 1000 element crossbar switch). The energy required to switch the element must be small enough that the heat generated by reconfiguration of the whole device, within the desired time, does not generate more heat than can be feasibly dissipated. The elements must share control lines or in some way be addressable in parallel so that the number of control lines remains small compared to the number of signal lines. The elements must be manufacturable by techniques that produce all the elements needed for a complete device in parallel so that the cost of the device in not prohibitive.

Conventional electro-optic materials (e.g., $LiNbO_3$) can switch in a few picoseconds but are only weakly birefringent and thus require long optical interaction lengths or high drive voltage which produces large switching energy to achieve required high contrast. Most other optical switching materials suffer from similar shortcomings.

Most effort in the development of FLC materials has been directed towards flat panel display applications. The optimal characteristics for FLC materials used in such displays include high spontaneous polarization and low orientation viscosity which are required to achieve fast switching, tilt angles of 22.5 which result in maximum contrast between crossed polarizers, low birefringence which facilitates construction of a desirable thickness panel and broad temperature range of the desired FLC phase.

Unfortunately, several of these parameters are far from optimal for FLC materials useful in waveguides, integrated optics, and spatial light modulators. High polarization and low viscosity are desired for both display and optical switching FLC applications. However, enhanced performance in optical switching applications is correlated with high total refractive index change between the switched states which is associated with high birefringence and large tilt angles.

A particular type of FLC display device, a dichroic display device containing color switching elements incorporating mixtures of FLCs with dichroic dyes, also requires high tilt FLC material (tilt angle of 45°) to achieve highest contrast (see Ozaki et al. (1985) Jpn. J. Appl. Phys. Part I 24 (Suppl. 24-3):63–65).

A basic requirement for application of ferroelectric liquid crystals in any device is the availability of chemically stable liquid crystal materials which exhibit ferroelectric phases over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing chiral smectic C* phases with useful temperature ranges can also be obtained by admixture of chiral, nonracemic compounds, designated ferroelectric liquid crystal dopants, into a liquid crystal host material (which may or may not be composed of chiral molecules). Addition of the dopant can affect the ferroelectric polarization density and/or the viscosity of the C* phase and thereby affect the switching speed. To achieve fast switching, desirable FLC dopants are molecules which impart high ferroelectric polarization density to an FLC material without significantly increasing the orientational viscosity of the mixture. For applications requiring high tilt angle materials it is desirable to have FLC materials which combine the properties of high tilt angle with fast switching speed and broad room temperature smectic C* phases.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains an (S)-2-methylbutyloxy chiral tail. Pure DOBAMBC exhibits a smectic C* phase with a ferroelectric polarization of $-3$ nC/cm$^2$.

The structures and polarization of several known smectic C* materials, including several containing phenylbenzoate cores, have been summarized in Walba et al. (1986a) J. Amer. Chem. Soc. 108:5210–5221, which also discusses a number of empirical correlations between molecular structure and FLC properties.

There are several reports of compounds containing phenylbenzoate and related cores coupled to chiral tail units which possess monotropic smectic C* phases displaying fast switching speeds at room temperature, or which can be employed as FLC dopants to induce high polarization and fast switching speeds when combined in mixtures with FLC host materials. Walba et al., U.S. Pat. No. 4,556,727 reports phenylbenzoates having nonracemic 2-alkoxy-1-propoxy tails. Eidman and Walba, U.S. Pat. No. 4,777,280 reports chiral 1-cyanoalkoxy phenylbenzoates. Walba and Razavi, U.S. Patent 4,695,650 reports chirally asymmetric reverse ester phenylbenzoates having chiral 1-haloalkyl tail units. Wand and Walba, U.S. patent application Ser. No. 164,233, filed Mar. 4, 1988, now allowed reports chirally asymmetric FLC materials having 2-haloalkoxy, 2,3-dihaloalkoxy or 2,3,4-trihaloalkoxy tails incorporated into a suitable core such as those based on biphenyl, phenylbenzoate, biphenylbenzoate or phenylpyrimidine moieties.

Walba and Razavi, U.S. Pat. No. 4,835,295 filed Sept. 21, 1987, discloses chirally asymmetric phenyl- and biphenylbenzoates having chiral 2,3-epoxy alkyl or 1-halo-2,3-epoxy alkyl tails which are useful for the preparation of FLC materials which possess smectic C* phases and have high polarization density. Tilt angles of the smectic C* phases of these FLC mat®rials have not been reported.

Walba et al. (1986) J. Amer. Chem. Soc. 108:7424–7425 and Walba and Vohra, U.S. Pat. Nos. 4,648,073 and 4,705,874 disclose ferroelectric smectic liquid crystal compounds possessing a high ferroelectric polarization density having chiral tail units derived from (2,3) alkyloxiranemethanols and achiral phenylbenzoate and biphenyl core units. The ferroelectric crystal compounds reported have the following general formulas:

where R is an alkyl of one to seven carbon atoms and R' is an alkyl of five to twelve carbon atoms and Ar is phenylbenzoate or biphenyl. Tilt angles of the smectic C* phases of these FLC materials have not been reported.

Hemmerling et al. (1988) European Patent Application, Pub. No. 263437 refers to chiral aryl-2,3-epoxyalkylether FLC compounds having phenylpyrimidine or phenylpyridazine cores of the formula:

where A is a diazine-2,5,-diyl or diazine-3,6-diyl, $R^4$ includes straight chain or branched alkyl groups and $R^1$ includes straight chain or branched alkyl groups having one to twelve carbons. The properties, including tilt angle, of several FLC mixtures containing certain of these compounds are provided. All of the FLC mixtures described have tilt angle less than 30°.

Ichihashi et al. (1988) European Patent Application, Pub. No. 269062 describes FLC compositions reported to have tilt angles between 30 to 60. and superior alignment properties. The authors state that most known FLC compounds (single component materials) having a high tilt angle , i.e. greater than or equal to 30° in the smectic C* phase, do not posses a higher temperature smectic A phase, while those having such a smectic A phase have low tilt angle, i.e. less than 30°. It is, thus, inferred that tilt angle depends on the ordering of phases, in particular on the type of phase occurring above the C* phase. It is reported that high tilt smectic C* compositions which posses a higher temperature smectic A phase can be obtained by admixture of a chiral or achiral smectic C compound also having a smectic A phase having a temperature range within 40° C. with a chiral smectic C compound having no smectic A phase. The presence of a smectic A phase is described as useful for alignment of an FLC material. The authors also report that tilt angle of a composition is an approximately additive function of the tilt angles of the individual components. Although the tilt angles of a number of smectic C compounds including several having phenylbenzoate and related cores are reported, no correlation between tilt angle and chemical structure is noted.

In a related reference, Furukawa et al. (1988) European Patent Application Pub. No. 220747 refers to a method for controlling the tilt angle in ferroelectric smectic C mixtures. The reference contains a list of FLC compounds, including a number of compounds having phenylbenzoate and related cores, giving phase diagrams and in many cases tilt angles. This reference also refers to the correlation between the presence of smectic A phases with tilt angles less than 30°. A method for controlling the tilt angle of an FLC mixture by adjusting the composition of the mixture such that a smectic A phase is present (for low tilt angle mixtures) or absent (for high tilt angle mixtures).

SUMMARY OF THE INVENTION

It is an object of this invention to provide FLC compositions having high polarization density which is associated with fast switching speeds. It is a particular object of this invention to provide FLC compositions having high polarization density and high tilt angle, i.e. greater than about 30°, which are useful, for example, in optical switching devices and dichroic display devices.

The present invention provides a class of nonracemic chirally asymmetric molecules which are useful for the preparation of high polarization density FLC compositions. These compounds result from the incorporation of enantiomerically enriched (2,3)-alkyloxiranemethanols tail units into achiral three ring phenyl-(phenylbenzoate) or biphenylbenzoate core moieties having the following structure:

where Ph is a 1,4 substituted phenyl group, m=2 and n=1 or m=1 and n=2, asymmetric carbons are indicated by *, R is an alkyl group having three to fifteen carbon atoms, and R' is an alkyl group having one to seven carbons.

Those compounds in which the asymmetric carbons of the epoxide tail have R,R or S,S configuration are preferred. The R alkyl substituent can be straight chain or branched, and if branched, can contain one or more asymmetric carbons. Racemic or chiral nonracemic branched R groups having asymmetric carbons can be employed. If the R group is branched at the 1-position, it is preferred that the chiral non-racemic group having the same sign of the polarization as the chiral epoxide group be employed, i.e. a branched 1(S) R group would preferably be employed with the (2R,3R) epoxide tail. It is preferred that the R be an alkyl group having from five to twelve carbon atoms. Straight chain R groups having eight to ten carbons are more preferred. The branched R groups: dimethyloctyl-, methylheptyl-, methylhexyl-, methyloctyl-, and methylbutyl- are more preferred, particularly the 3,7 dimethyloctyl-, 1-methylheptyl-, 4-methylhexyl, 6-methyloctyl and 2-methylbutyl- groups are more preferred. It is preferred that R' be an alkyl group having one to three carbon atoms, with the n-$C_3H_7$ group being more preferred.

The invention specifically provides the chiral non-racemic biphenylbenzoate epoxides (I, where m=1 and n=2), wherein the predominant enantiomer is 4-4'[p-(2R,3R-epoxy)hexyloxy]biphenyl-p-n-octyloxybenzoate, herein designated MDW 102; 4-4'[p-(2R,3R-epoxy)hexyloxy]biphenyl-p-n-nonyloxybenzoate, herein designated MDW 95; 4-4'[p-(2R,3R-epoxy)hexyloxy]biphenyl-p-n-decyloxybenzoate, herein designated MDW 94; 4-4'[p-(2R,3R-epoxy)hexyloxy]biphenyl-p-3S,7-dimethyloctyloxybenzoate, herein designated MDW 100; 4-4'[p-(2S,3S-epoxy)hexyloxy]biphenyl-p-1S-methylheptyloxybenzoate, herein designated MDW 112; 4-4'[p-(2R,3R-epoxy)hexyloxy]biphenyl-p-4S-methylhexyloxybenzoate, herein designated MDW 113; 4-4'[p-(2R,3R-epoxy)hexyloxy]biphenyl-p-6S-methyloctyloxybenzoate, herein designated MDW 114; 4-4'[p-(2R,3R-epoxy)hexyloxy]biphenyl-p-2S-methylbutyloxybenzoate, herein designated MDW 133; 4-4'[p-(2R,3R-epoxy)hexyloxy]biphenyl-p-1S-methylheptyloxybenzoate, herein designated MDW 153. Each of the preceding specific compounds was prepared essentially free of diastereomeric contaminants.

The invention specifically provides the chiral non-racemic (phenyl)-phenylbenzoate epoxides, wherein the predominant enantiomer is 4-4'[p-(2R,R-epoxy)hexyloxyphenyl]phenyl-p-n-octyloxybenzoate, herein designated MDW 99; 4-4'[p-(2R,R-epoxy)hexyloxyphenyl]phenyl-p-3S,7-dimethyloctyloxybenzoate, herein designated MDW 127; 4-4'[p-(2R,R-epoxy)hexyloxyphenyl]phenyl-p-1S-methylheptyloxybenzoate, herein designated MDW 175.

In addition to the property of high polarization, the epoxy phenylbenzoates of the present invention display a novel property of inducing a tilt angle greater than expected in FLC compositions in which they are combined. It has been taught that the tilt angle of a composition is an approximately additive function of the tilt angle of the individual components times the weight percent of the component in the composition. FLC mixtures containing the phenylbenzoate epoxides of the present invention have tilt angles greater than expected based on this teaching, and thus act to induce higher tilt in FLC mixtures. It was found that phenylbenzoate epoxides having branched R groups were particularly effective for induction of high tilt. The ability to achieve high tilt FLC mixtures by employing unexpected low amounts of high tilt inducers allows more flexibility in the kind and amounts of components that can be incorporated in high tilt mixtures. For example, it is now possible, employing the high tilt inducers of the present invention, to obtain high tilt mixtures which contain larger amounts of low tilt materials than expected. It can be desirable to include such low tilt materials in high tilt mixtures to obtain other desirable properties. High tilt materials, i.e. those having a tilt angle greater than about 30°, which are, for example, suitable for dichroic displays, can be made by admixture of lower than expected amounts of the branched R group phenylbenzoate epoxide high tilt inducers with low tilt (i.e., less than about 26°) materials. Further, the high tilt materials prepared employing the high tilt inducers of the present invention have high polarization density that is associated with fast switching speeds. The degree of high tilt induction observed in mixtures with branched R group phenylbenzoate epoxides can vary with the type of low tilt material combined in the mixture.

Chiral, non-racemic three-ring phenylbenzoate epoxides having the formula:

where R is a branched alkyl group having three to fifteen carbon atoms, R' is an alkyl group having one to seven carbons, Ph is a 1,4 substituted phenyl group, m=2 and n=1 or m=1 and n=2, and asymmetric carbons are indicated by * have the property of high tilt induction. Further, these compounds also have high polarization density that is associated with fast switching speeds.

For high tilt induction and high polarization density, those compounds having the chiral trans-epoxide tail, with an R,R or S,S configuration, at the asymmetric carbons are preferred. It is preferred that R' be an alkyl group having one to three carbon atoms, with the n-$C_3H_7$ group being more preferred. High tilt induction is associated with branched alkyl R groups. The branched R group can contain one or more asymmetric carbons. Racemic or chiral non-racemic branched R groups can be employed. If the R group is branched at the 1-position, it is preferred that the chiral non-racemic group having the same sign of polarization as that of the chiral epoxide group be employed. It is preferred that the R be an alkyl group having from five to twelve carbon atoms. The branched R groups: dimethyloctyl-, methylheptyl-, methylhexyl-, methyloctyl-, and methylbutyl- and particularly the 3,7 dimethyloctyl-, 1-methylheptyl-, 4-methylhexyl, 6-methyloctyl and 2-methylbutyl-groups are more preferred.

The phenylbenzoate epoxides with branched R groups having the structure:

where Ph is a 1,4 substituted phenyl group and R' is an alkyl group having one to seven carbon atoms, and asymmetric carbons are indicated by *, also displayed high tilt induction. Certain of these compounds had been previously described as FLC compounds having high polarization density; however, these compounds were not previously described as high tilt inducers.

For high tilt induction and high polarization density, those compounds having the chiral trans-epoxide tail, with an R,R or S,S configuration, at the asymmetric carbons are preferred. It is also preferred that R' be an alkyl group having one to three carbon atoms, with the n-$C_3H_7$ group being more preferred. High tilt induction is associated with branched alkyl R groups. The branched R group can contain one or more asymmetric carbons. Racemic or chiral non-racemic branched R groups can be employed. If the R group is branched at the 1-position, it is preferred that the chiral non-racemic group having the same sign of polarization as that of the chiral epoxide group be employed. It is preferred that the R be an alkyl group having from five to twelve carbon atoms. The branched R groups: dimethyloctyl-, methylheptyl-, methylhexyl-, methyloctyl-, and methylbutyl- and particularly the 3,7 dimethyloctyl-, 1-methylheptyl-, 4-methylhexyl, 6-methyloctyl and 2-methylbutyl-groups are more preferred.

Specifically this invention provides the following chiral nonracemic high tilt inducers, in which the predominant enantiomer is p-(2R,R-epoxy)hexyloxyphenyl-p-3S,7-dimethyloctyloxybenzoate, herein designated MDW 74; p-(2S,S-epoxy)hexyloxyphenyl-p-1S-methylheptyloxybenzoate, herein designated MDW 93; p-(2R,R-epoxy)hexyloxyphenyl-p-1S-methylheptyloxybenzoate, herein designated MDW 152; and the compounds designated MDW 100, MDW 112, MDW 113, MDW 114, MDW 127, and MDW 153 the specific structures of which are provided above.

The chirally asymmetric high tilt inducers of the present invention need not themselves possess a smectic C* phase. It was found that certain of the two- and three-ring phenylbenzoate epoxides having the structural features described above and incorporating branched R groups did not in pure form possess a smectic C* phase. These compounds, nevertheless, displayed high tilt induction when mixed with certain low tilt materials.

In a second aspect, the present invention provides a method for preparing FLC mixtures having tilt angles greater than expected by incorporating a high tilt inducer of the present invention in a mixture. In particular, a method is provided for preparing FLC mixtures having tilt angles greater than about 30° by mixing a high tilt inducer with a low tilt material. Employing the high tilt inducers of the present invention, it is now possible to prepare high tilt mixtures in which the major component (50% or greater) of the mixture is a low tilt material. For example, combination of from about 2 to 50 weight % of a high tilt inducer with a low tilt material having a tilt angle of 15° or less can result in a high tilt material; combination of from about 2 to 40 weight % of a high tilt inducer with a low tilt material having a tilt angle of 20° or less can result in a high tilt material; combination of from about 2 to 21 weight % of a high tilt inducer with a low tilt material having a tilt angle of 26° or less can result in a high tilt material. Since tilt angle of a mixture is expected to be an additive function of the tilt angles of the components times the weight % of the component in the mixture and since there are very few reports of compounds having a tilt angle greater than 45°, prior to the present work it would not have been anticipated that any high tilt mixtures containing such high percentages of low tilt material as described above could be prepared.

DETAILED DESCRIPTION OF THE INVENTION

Figure 1:
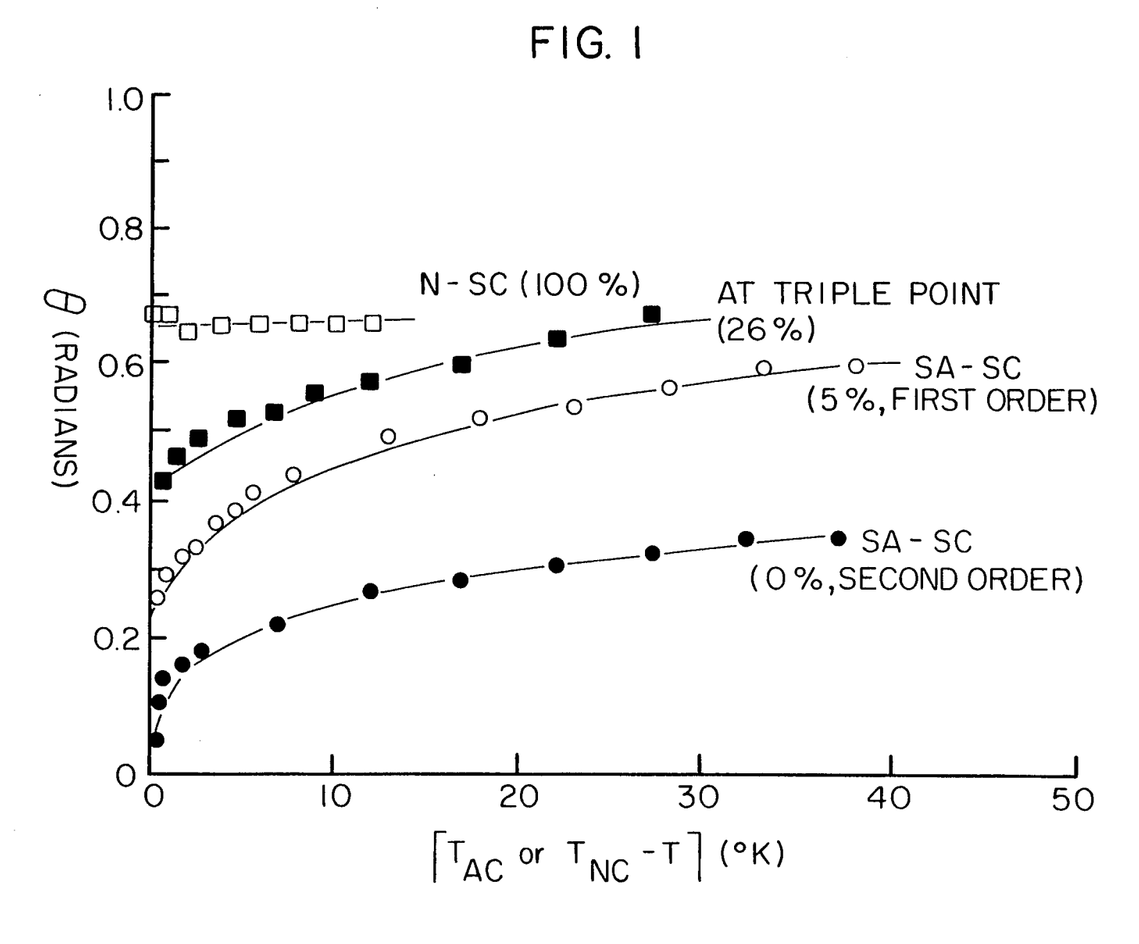
FIG. 1 is a plot of tilt angle (Θ) given in radians (360°=2π radians) in mixtures of MDW 74 in W82 as a function $T_c-T$, where $T_c$ is the upper transition temperature of the C phase, for several mixtures varying in composition (5% (w/w) MDW 74 and 26% (w/w) MDW 74). Tilt angle increases rapidly and achieves saturation (38°) on addition of relatively small amounts (5%) of MDW 74.

The two and three ring epoxides of the present invention are prepared as described in the exemplary Scheme 1:

SCHEME 1

-continued
SCHEME 1

Chiral, nonracemic phenylbenzoate epoxides having a variety of alkyl R and R' groups can be readily synthesized employing the methods of Scheme I. Starting materials are readily available either from commercial sources or through synthesis by conventional well-known methods.

Table 1 provides liquid crystal properties of a number of two- and three-ring phenylbenzoate epoxides with straight chain and branched R groups. Many of the pure components possess a smectic C* phase having a high tilt angle. Liquid crystal phases are designated as follows: X=crystal, C*=chiral smectic C, N*=chiral smectic N, A=smectic A, I=isotropic liquid.

The present invention is based in part on the discovery that certain FLC compounds incorporating a chirally asymmetric epoxymethanol tail group associated with high polarization density and a branched or alkoxy tail group induce unexpectedly high tilt in FLC compositions (Table 2). The high tilt angles observed in the FLC compositions of the present invention were surprising since it has been reported that the smectic C* phase tilt angle of FLC compositions is an approximately additive function of the tilt angles of the individual components of the composition (Ichihashi et al. (1988) European Patent Application Pub. No. 269062). Thus it was taught that when two compounds A and B, which display smectic C phase tilt angles of $\Theta_A$ and $\Theta_B$, respectively, were combined to form a smectic C phase two component mixture that the tilt angle of the mixture, $\Theta_{mix}$ could be calculated by the equation:

$$\Theta_{mix} = \text{weight \%} A \times \Theta_A + \text{weight \%} B \times \Theta_B$$

Similar calculations would have been expected to apply to mixtures having more than two components. Tilt angle of mixtures containing the high tilt inducers of the present invention are higher than expected based on this calculation.

Table 2 provides liquid crystal properties of illustrative mixtures of a number of phenylbenzoate epoxides with the low tilt material W82. In the mixtures exemplified in Table 2, the weight percent of phenylbenzoate is low (10%).

W82 (XI)

A 10:90 (W:W) mixture of the branched p-2R, 3R-epoxyhexyloxyphenyl-3S,7-dimethyloctyloxybenzoate (vIII where R=3S,7-dimethyloctyloxy and R'=n-propyl), designated MDW 74, in the low tilt FLC host material W82 (XI) possessed a smectic C* phase having a high tilt angle of 38°. MDW 74 is itself a high tilt FLC compound having a C* phase with a 38° tilt angle (Table 1), while W82 is a chiral low tilt angle material with a tilt angle of 18° The calculated tilt angle for a 10:90 mixture of these two materials would be expected to be only about $(0.1 \times 38 + 0.9 \times 18)$ or 20° which is much lower than the observed tilt angle.

For comparison, a 10:90 (w:w) mixture of the straight chain p-(2R,3R)-epoxyhexyloxyphenyl-n-octyloxybenzoate (VIII where R=n-$C_{10}H_{21}$ and R'=n-propyl), designated W46 in W82, has a low tilt angle of 27°. As indicated in Table 2, induction of tilt higher than about 30° is associated with branched R groups in a position on the core opposite to the epoxide tail.

High tilt induction is not a general property of FLC compounds having branched R groups. Table 3 pro- vides tilt angle data for FLC mixtures of non-epoxide branched R group phenylbenzoates in W82. None of the compounds listed in Table 3 exhibits tilt over 30°.

Data in Table 4 illustrate the properties of FLC mixtures prepared using the high tilt inducer MDW 74. Included in Table 4 are data for mixtures of MDW 74 in several commercially available FLC host materials, as well as data for mixtures containing more than two components.

ZLI-3234B is an achiral host material known to possess an enantiotropic smectic C phase which was obtained from E. Merck. This host material has been described in Geelhaar (1988) Ferroelectrics 85:329–349 and Escher et al (1988) Liquid Crystals 3(4):469–484. It is our understanding that ZLI3234B is a mixture of achiral phenylpyrimidines, designated NCBs, which have an axial cyano group substituted on a cyclohexyl ring and have the general structure:

where R is an alkyl or alkoxy group and R' is an alkyl group. The phase diagram of ZLI3234B is:

ZLI4003 is a low tilt (25°) material available from E. Merck which is believed to be a mixture of about 10 components. The material is reported to suppress the low end of the C phase and broaden the C phase. CS2002 is a commercial high tilt FLC material available from BDH (England). The composition of CS2002 is unknown to applicants. SCE12 is a low tilt material available from Chisso (Japan) which is believed to be composed primarily of laterally fluorinated phenylbenzoates.

The term tilt angle as used herein refers to the saturation tilt angle of a smectic C or chiral smectic C phase. Tilt angle varies with temperature near the transition point between the C phase and the higher temperature (A or N*) phase. Tilt angle can rapidly increase reaching saturation within a few degrees in temperature from the transition point (first order behavior) or tilt angle can more slowly increase reaching saturation within 10°–20° C. below the transition temperature (second order behavior). Tilt angles provided herein are measured at $T_c - T$ and are saturation tilt angles. $T_c$ and $T_x$ are the upper and lower transition temperatures for the smectic C phase, respectively.

High tilt as used herein refers to materials particularly suitable for dichroic displays with tilt angle greater than about 30°. Low tilt as used herein refers to materials having tilt angles less than about 26°. Low tilt materials can be mixtures of one or more components in which the tilt angle of the mixture is less than about 26°.

It will be appreciated by those in the art that the high tilt inducers of the present invention will not mix with all FLC host materials. FLC host materials useful with the high tilt inducers of the present invention must have compatible mixing properties, i.e. be capable of mixing with one another. Mixtures useful for FLC applications must possess a smectic C* phase. Phase diagrams of mixtures often change as a function of composition. Those in the art know how to determine which components and host materials are compatible for mixing and how to assess phase behavior of mixtures. Data in Table 4 indicate that the high tilt inducers of the present invention may not induce high tilt in combination with all FLC guest materials. For example, MDW 74 did not induce high tilt in a 20% mixture with ZLI-4003. Those in the art can readily ascertain whether or not the high tilt inducers of the present invention will induce high tilt in a particular host material using procedures similar to those described herein.

EXAMPLES

Example 1

Synthesis of Substituted Epoxyphenols (II, where n=1 or 2)

The epoxyphenols of the present invention are prepared by a modification of the methods described in Walba and Vohra U.S. Pat. No. 4,648,073 by coupling of 4-benzyloxyphenol (IV, n=1) or p-hydroxy-4-benzyloxybiphenyl (IV, n=2) with an appropriate chiral epoxy tosylate (III) followed by debenzylation of the resulting coupling product. The method is exemplified for the synthesis of p-hydroxy[(2R,3R)-epoxy]hexyloxy-4-4'-biphenyl (V, where n=2 and R'=n-C₃H₇).

Synthesis of p-Hydroxy[(2R,3R)-epoxy]hexyloxy-4-4'-biphenyl p-Hydroxy-4-benzyloxybiphenyl (0.97 g) and NaH (0.8 g) were added to a mixture of 30 ml of dry THF and 5 ml of dry DMF in a three-neck, vacuum dried flask that had been flushed with dry nitrogen and was fitted with a magnetic stir bar. The resulting mixture was stirred for about 30 min to allow complete reaction of the NaH to generate the phenoxide. (2R,3R)-3-propyloxirane methyl tosylate (0.95 g) was then added and the resulting reaction mixture was refluxed gently for 4 hr. The reaction mixture was then extracted with ether. The ether layer was washed first with dilute NaOH to remove unreacted phenol and then with brine. The washed ether layer was dried over MgSO₄ and filtered. Ether was removed in vacuo and the residue purified by passage through a short silica column eluting with 25% (v/v) ethyl acetate in hexanes to give 0.98 g (75% yield) of p-benzyloxy[(2R,3R)-epoxy]hexyloxy-4-4'-biphenyl.

p-Benzyloxy[(2R,3R)-epoxy]hexyloxy-4-4'-biphenyl (0.98 g) and 200 mg of Pd(OH)₂ 10% (w/w) on carbon were added to 100 ml of ethanol in a glass hydrogenator fitted with a magnetic stir bar. Hydrogen gas was then introduced into the reaction vessel and the reaction mixture was stirred at about 50° C. until all of the starting biphenyl had reacted. The reaction mixture was then filtered through a thick pad of celite and ethanol was removed in vacuo to give the product p-hydroxy[(2R,3R)-epoxy]hexyloxy-4-4'-biphenyl (0.71 g, 92% yield).

EXAMPLE 2

Synthesis of Substituted Benzyl chlorides (VII where m=1 or 2)

The substituted benzyl chlorides of the present invention are prepared, for example, by reaction of substituted acetophenone (VI) with the tosylate of the desired alcohol (ROH) which may be straight-chain or branched and can be a racemic or chiral non-racemic alcohol. The method is exemplified by the synthesis of 1S-methylheptyloxybenzoyl chloride (VII, where m=1 and R=1S-methylheptyl).

Synthesis of 1S-Methylheptyloxybenzoylchloride p-Hydroxyacetophenone (7.48 g) was added to 100 ml of isopropanol containing 3.63 g of KOH. The mixture was stirred at room temperature for 20 minutes after which 1S-methylheptyl tosylate (14.2 g) was added. The resulting mixture was refluxed for 6 hrs after which the solvent was removed. The reaction residue was partitioned between ether and water and the ether layer was collected and washed with dilute NaOH until no hydroxy acetophenone was detected by thin layer chromatography. The washed ether layer was then washed sequentially with water and brine and the ether was removed in vacuo to give 1S-methylheptyloxy acetophenone (10.6 g, 85% yield).

A NaOBr solution was prepared by dissolving NaOH (37.4 g) in 200 ml of water and the solution was cooled to 0° C. Bromine (Br$_2$, 9.4 ml) was then added to the cooled solution slowly so that the temperature of the mixture did not rise above 5° C. 1S-methylheptyloxyacetophenone (10.6 g) was dissolved in 100 ml of dioxane and the NaOBr solution was added dropwise to the reaction mixture over 30 min. at room temperature. The reaction mixture was then stirred overnight at room temperature. Water (150 ml) was then added to the reaction mixture and the resultant mixture was partitioned between water and ether. Since the reaction mixture was basic, the product benzoic acid, as the Na salt, was in the water layer. The ether layer was washed with dilute NaOH to dissolve any remaining product. The aqueous layers were combined and acidified to precipitate the product benzoic acid. The precipitate was re-extracted using ether, the ether layer was collected and dried over MgSO$_4$ and filtered. Ether was then removed in vacuo to give the crude benzoic acid product, which was then recrystallized from ethanol to give 6.5 g of 1S-methylheptyloxybenzoic acid.

1S-methylheptyloxybenzoic acid (1.0 g) was dissolved in 10 ml of toluene and 0.48 g of oxalylchloride was then added to the resulting solution. The reaction mixture was then refluxed for 2 hrs, after which toluene and excess oxalyl chloride were removed in vacuo resulting in the product acid chloride, 1S-methylheptyloxybenzoylchloride.

EXAMPLE 3

Synthesis of Substituted Epoxides (VIII - X where m, n=1, m=1, n=2 or m=2, n=1)

The substituted epoxide, FLC materials of the present invention are prepared by coupling of the epoxyphenols (v) with the benzoyl chlorides (VII). The method is exemplified by the synthesis of p-[(2R,3R-epoxy)hexyloxyphenyl](3S, 7-dimethyl)octyloxybenzoate, designated MDW74 (VIII, where n=1, m=1, R'=n-C$_3$H$_7$ and R=3S, 7-dimethyloctyl) and 4-4'-[p-[(2R,3R-epoxy)hexyloxy]biphenyl-p-1S-methylheptyloxybenzoate, 1S-methylheptyloxy).

Synthesis of p-[(2R,3R-epoxy)hexyloxyphenyl](3S-methyl,7-dimethyl)octyloxybenzoate 3S,7-dimethyloctyloxybenzoylchloride (6.00 g, 20.2 mmoles) and p-(2R,3R-epoxy)hexyloxyphenol (4.20 g, 20.2 mmoles) were dissolved in 50 ml of dry, cold (0° C.) THF and a catalytic amount of dimethylaminopyridine (DMAP) was added to the solution. Triethylamine (3.0 g) was then added dropwise to the cold reaction mixture, after which the reaction mixture was warmed to room temperature and stirred until reaction was complete. The solvent was then remove in vacuo and the resulting residue was partitioned between ether and water. The ether layer was washed with dilute HCl to remove excess triethylamine and DMAP, dried over MgSC$_4$ and filtered. Crude product was obtained by removing ether in vacuo. The crude product was then purified by flash chromatography on a silica gel column using 3% (v/v) ethyl acetate/hexanes as an eluant to give the 8.13 g (86% yield) of purified product.

Synthesis of 4-4'[p-[(2S,3S)-epoxy]hexyloxy]biphenyl-p-1S-methyl heptyloxy benzoate p-1S-methylheptyloxy benzoylchloride (127 mg) and p-hydroxy[(2S,3S)-epoxy hexyloxy]biphenyl (142 mg) were dissolved in 5 ml of dry, cold (0° C.) THF in a 25 ml flask. A catalytic amount of dimethylaminopyridine and 0.3 ml of triethylamine were then added to the cold reaction mixture. The resultant mixture was stirred for 4 hr, after which the solvent was removed. The residue was partitioned between water and ether. The ether layer was washed with dilute HCl to remove excess triethylamine, dried over MgSO$_4$ and filtered. Ether was then remove in vacuo to give the crude product which was purified by flash chromatography on a silica gel column eluting with 5% (v/v) ethyl acetate/hexanes to give 4-4'-[p-[(2S,3S)-epoxy]hexyloxy]biphenyl-p-1S methyl heptyloxy benzoate (180 mg, 74% yield). If desired, the product can be further purified by recrystalization from hexanes.

EXAMPLE 4

Phase Behavior of FLC materials

Exemplary phase diagrams of the FLC materials of the present invention are summarized in Table 1. The phase diagrams of exemplary mixtures of epoxy phenylbenzoates FLC compounds in mixtures with FLC host materials are given in Tables 2 and 3. The phase transition temperatures and the nature of the phase transition were determined using Mettler Differential Thermal Analysis (DTA) and optical polarized transmission microscopy. Director tilt angles in the C phases were determined optically.

TABLE 1

Liquid Crystal Properties of Two and Three Ring Phenylbenzoate Epoxides[1]

RO—(Ph)$_m$—CO$_2$—(Ph)$_n$—OCH$_2$—CH———CH-n-C$_3$H$_7$

| Designation # | R | m | n | *, * | phase diagram | tilt[2] | Ps[2] |
|---|---|---|---|---|---|---|---|
| W46 | n-C$_{10}$H$_{21}$ | 1 | 1 | R, R | X 75 I* 65 C* 83 N* 102 I | 29 | 45 |
| MDW 74 | 3S, 7 DMO | 1 | 1 | R, R | X 30 C* 45 N* 55I | 38 | 113 |
| MDW 93 | 1S MH | 1 | 1 | S, S | X 35 I | | |

TABLE 1-continued

Liquid Crystal Properties of Two and Three Ring Phenylbenzoate Epoxides[1]

| Designation # | R | m | n | *,* | phase diagram | tilt[2] | Ps[2] |
|---|---|---|---|---|---|---|---|
| MDW 99 | n-$C_8H_{17}$ | 2 | 1 | R, R | X 132 C* 180 A 184 N* 209 I | | |
| MDW 102 | n-$C_8H_{17}$ | 1 | 2 | R, R | X 113 C* 165 N* >200 I | 40 | 48 |
| MDW 95 | n-$C_9H_{19}$ | 1 | 2 | R, R | X 117 C* 174 N* 212 I | 40 | 38 |
| MDW 94 | n-$C_{10}H_{21}$ | 1 | 2 | R, R | X C* N* I | | |
| MDW 100 | 3S, 7 DMO | 1 | 2 | R, R | X 110 I* 120 C* 159 N* 165 I | 37 | |
| MDW 112 | 1S MH | 1 | 2 | S, S | X 65 C* 124 N* 148 I | | |
| MDW 113 | 4S MHX | 1 | 2 | R, R | X 102 C* >149 N* I | | |
| MDW 114 | 6S MO | 1 | 2 | R, R | X 110 I* 120 C* >145 N* I | | |
| MDW 127 | 3S, 7 DMO | 2 | 1 | R, R | X 77 C* 155 N* 175 I | 35 | 79 |
| MDW 133 | 2S MBu | 1 | 2 | R, R | X C* 136 N* 203 I | | |
| MDW 153 | 1S MH | 1 | 2 | R, R | X 85 C* 136 N* 155 I | 36 | 149 |
| MDW 152 | 1S MH | 1 | 1 | R, R | X <20 I | | |
| MDW 175 | 1S MH | 2 | 1 | R, R | X 60 C* 120 N* 145 I | 38 | 67 |

[1]All data are for the chiral noracemic trans-epoxides having the indicated configuration; DMO = dimethyloctyl; MH = methylheptyl; MHx = methylhexyl; MO = methyloctyl; MBu = methylbutyl
[2]Measured at Tc-Tx, where Tc and Tx are the upper and lower temperatures of the C* phase, respectively.

TABLE 2

Induction of high tilt with 10% dopant in host W82 (natural 18° tilt)
W82 phase diagram (X 35 C* 70 A 74 I)[1]

| Dopant | tilt of 10% mixture | Phase Diagram |
|---|---|---|
| W46 | * 27 | X 32 C* 69 A 71 N* 78 I |
| MDW 74 | ** 38 | X C* 69 A 71 N* 72.5 I |
| MDW 93 | ** 32 | X C* 66 A N* I |
| MDW 102 | * 26 | X 35 C* 75.3 A 77.3 N* 84.5 I |
| MDW 95 | * 25 | X 35.6 C* 73.3 A 76.6 N* 82.5 I |
| MDW 100 | ** 30 | X 32.0 C* 76.4 A 77.2 N* 81.3 I |
| MDW 112 | ** | X 15 B 24 C* 75 A 76 N* 115 I |
| MDW 113 | ** 30 | X 34.5 C* 76.3 A 76.9 N* 83.2 I |
| MDW 114 | ** 32 | X 35.5 C* 76.5 A 77.2 N* 82.2 I |
| MDW 152 | ** 38 | X 24.1 C* 66.5 A 68.2 N* 71.4 I |
| MDW 153 | ** 34 | X 30 C* 77.1 N* 80.8 I |
| MDW 127 | ** 32 | |

[1]Tilt angles are measured at room temperature;
*straight chain and
**branched chain

TABLE 3

Mixtures of Non-epoxide Branched R Tail FLC's in W82
RO-(Ph)-$CO_2$-(Ph)$_n$-OR'

| Dopant[1] | Tilt (weight % dopant) | phase diagram |
|---|---|---|
| SMC 8-7 (7*0.7) where n = 1, R = 4S MHz R' = n-$C_7H_{15}$ | 24 (10%) | X <23 C* 67.6 A 70.3 N* 72.1 I |
| SMC 10 9 (9*0.9) where n = 1, R = 6S MO R' = n $C_9H_{19}$ | 25 (10%) | X 29.0 C* 70.3 A 71.7 N* 73.2 I |
| PC6benzoate where n = 2, R = 1S MH R' = n-$C_6H_{13}$ | 23 (10%) | |
| MDW 120 where n = 1, R = 1S MH R' = (S)—CO—CH(Cl)—C($CH_3$)$_2$ | 27 (10%) | |

TABLE 4

Tilt Induction of MDW 74 in Various FLC Host Materials

| Host Material or Mixture | Host tilt | Induced tilt (Wt % MDW 74) | Calculated tilt |
|---|---|---|---|
| ZLI-3234B | 14 | 25 (10%) | 16.6 |
| | | 31 (20%) | 18.8 |
| ZLI-4003 | 23 | 26 (20%) | 26.0 |
| SCE 12 | 20 | 31 (20%) | 23.6 |
| CS 2002 | 31 | 35 (20%) | 32.4 |
| MX5002 (Host W82) | 18 | 38 (50%) | 28.0 |
| MX5162: | | 38 (45%) | 27.5 |
| 45% MDW 74 45% W82 10% ZLI 4003 | | | |
| MX5184: 37.5% MDW 74 37.5% W82 25% CS2002 | | 35 (37.5%) | 28.8 |

[1]Abbreviations are as in Table 1

We claim:

1. A chiral nonracemic compound of formula:

where R is an alkyl group having three to fifteen carbon atoms, R' is an alkyl group having one to seven carbons, Ph is a 1,4 substituted phenyl group, m=2 and n=1 or m=1 and n=2, and asymmetric carbons are indicated by *.

2. The compound according to claim 1 wherein m=1 and n=2.

3. The compound according to claim 2 wherein R is an alkyl group having five to twelve carbon atoms.

4. The compound according to claim 3 wherein R is a straight chain alkyl group having eight to ten carbon atoms.

5. The compound according to claim 3 wherein R is a branched alkyl group.

6. The compound according to claim 5 wherein the branched alkyl group is selected from the group consisting of dimethyloctyl, methylheptyl, methylhexyl, methyloctyl, and methylbutyl.

7. The compound according to claim 6 wherein the branched alkyl group is selected from the group consisting of 3,7 dimethyloctyl, 1-methylheptyl, 4-methylhexyl, 6-methyloctyl and 2-methylbutyl.

8. The compound according to claim 2 wherein R contains one or more asymmetric carbons.

9. The compound according to claim 8 wherein the R group is a chiral nonracemic group.

10. The compound according to claim 2 wherein R' is an alkyl group having three to seven carbon atoms.

11. The compound according to claim 10 wherein R' is n-propyl.

12. The compound according to claim 10 which is selected from the group of compounds consisting 4-4'[p-(2R,3R-epoxy)hexyloxy]biphenyl-p-n-octyloxybenzoate, 4-4'[p-(2R,3R-epoxy)hexyloxy]biphenyl-p-n-nonyloxybenzoate, 4-4'[p-(2R,3R-epoxy)hexyloxy]-biphenyl-p-n-decyloxybenzoate, 4-4'[p-(2R,3R-epoxy)hexyloxy]biphenyl-p-3S,7-dimethyloctyloxybenzoate, 4-4'[p-(2S,3S-epoxy)hexyloxy]biphenyl-p-1S-methylheptyloxybenzoate, 4-4'[p-(2R,3R-epoxy)hexyloxy]-biphenyl-p-4S-methylhexyloxybenzoate, 4-4'[p-(2R,3R-epoxy)hexyloxy]biphenyl-p-6S-methyloctyloxybenzoate, 4-4'-[p-(2R,3R-epoxy)hexyloxy]biphenyl-p-2S-methylbutyloxybenzoate, and 4-4'[p-(2R,3R-epoxy)hexyloxy]biphenyl-p-1S-methylheptyloxybenzoate.

13. The compound according to claim 10 which is selected from the group consisting of 4-4'[p-(2R,3R-epoxy)hexyloxy]-biphenyl-p-3S,7-dimethyloctyloxybenzoate, 4-4'[p-(2S,3S-epoxy)hexyloxy]biphenyl-p-1S-methylheptyloxybenzoate, 4-4'[p-(2R,3R-epoxy)hexyloxy]biphenyl-p-4S-methylhexyloxybenzoate, 4-4'[p-(2R,3R-epoxy)hexyloxy]biphenyl-p-6S-methyloctyloxybenzoate, 4-4'[p-(2R,3R-epoxy)hexyloxy]biphenyl-p-2S-methylbutyloxybenzoate, and 4-4'[p-(2R,3R-epoxy)hexyloxy]biphenyl-p-1S-methylheptyloxybenzoate.

14. The compound according to claim 1 wherein m=2 and n=1.

15. The compound according to claim 14 wherein R is an alkyl group having five to twelve carbon atoms.

16. The compound according to claim 15 wherein R is a straight chain alkyl group having eight to ten carbon atoms.

17. The compound according to claim 15 wherein R is a branched alkyl group.

18. The compound according to claim 15 wherein R is a dimethyloctyl or a methylheptyl group.

19. The compound according to claim 15 wherein R contains one or more asymmetric carbons.

20. The compound according to claim 19 wherein R is a chiral nonracemic group.

21. The compound according to claim 14 wherein R' is an alkyl group having three to seven carbon atoms.

22. The compound according to claim 21 wherein R' is n-propyl.

23. The compound according to claim 22 which is selected from the group consisting of 4-4'[p-(2R,R-epoxy)hexyloxyphenyl]phenyl-p-n-octyloxybenzoate, 4-4'[p-(2R,R-epoxy)hexyloxyphenyl]phenyl-p-3S,7-dimethyloctyloxybenzoate, and 4-4'[p-(2R,R-epoxy)hexyloxyphenyl]phenyl-p-1S-methylheptyloxybenzoate.

24. The compound according to claim 22 which is selected from the group consisting of 4-4'[p-(2R,R-epoxy)hexyloxyphenyl]phenyl-p-3S,7-dimethyloctyloxybenzoate, and 4-4'[p-(2R,R-epoxy)hexyloxyphenyl]phenyl-p-1S-methylheptyloxybenzoate.

* * * * *